United States Patent
Weizman et al.

(10) Patent No.: US 7,666,131 B2
(45) Date of Patent: Feb. 23, 2010

(54) PERI-ARTERIAL BLOOD FLOW BOOSTER

(75) Inventors: Gabi Weizman, Moshav Magen Shaul (IL); Aaron Hoffman, Haifa (IL)

(73) Assignee: Technion Research and Development Foundation Ltd., Haifa (IL)

( * ) Notice: Subject to any disclaimer, the term of this patent is extended or adjusted under 35 U.S.C. 154(b) by 271 days.

(21) Appl. No.: 10/560,825

(22) PCT Filed: Jun. 16, 2004

(86) PCT No.: PCT/IL2004/000520

§ 371 (c)(1),
(2), (4) Date: Mar. 13, 2006

(87) PCT Pub. No.: WO2004/110516

PCT Pub. Date: Dec. 23, 2004

(65) Prior Publication Data

US 2006/0183963 A1 Aug. 17, 2006

(30) Foreign Application Priority Data

Jun. 16, 2003 (IL) .................................... 156452

(51) Int. Cl.
*A61N 1/362* (2006.01)
(52) U.S. Cl. ........................................................ 600/17
(58) Field of Classification Search ............ 600/16–18; 251/5; 606/158
See application file for complete search history.

(56) References Cited

U.S. PATENT DOCUMENTS 3,675,656 A * 7/1972 Hakim .................... 606/158
4,256,094 A 3/1981 Kapp et al.
(Continued)

FOREIGN PATENT DOCUMENTS

DE 196 25 300 A1 1/1998
(Continued)

OTHER PUBLICATIONS

Kolff, W.J. "The Dawn of Counterpulsation. Muscle and Pneumatic Powered LVADs." ASAIO Journal; 1993, vol. 39, No. 4, pp. 825-827; Lippincott Williams & Wilkins/ ASAIO, Hagerstown, MD, US; XP000423346.

*Primary Examiner*—Mark W Bockelman
(74) *Attorney, Agent, or Firm*—The Nath Law Group; Susanne M. Hopkins; Ari G. Zytcer

(57) ABSTRACT

A peri-arterial blood flow booster apparatus for improving blood pressure and flow, to be implanted around a blood vessel of a patient. The booster comprises a pressure applying device (56) comprising at least one balloon (44), placed alongside a portion of the blood vessel and a restrainer (54) for restraining the balloon and providing counter-forces. It further comprises a control console (60) comprising: an inflating unit (66) for rapidly inflating and deflating the balloon, the inflating unit connected to the balloon; sensing means (68) for sensing electrocardiograph signals of the patient; a control unit (72) for controlling the operation of the inflating unit correlating to the electrocardiograph signals detected by the sensing means. When the balloon is inflated the restrainer forces it to compress the portion of the blood vessel preventing backflow and exerting forces on the blood vessel forcing blood within the portion of the blood vessel to flow antegradely.

20 Claims, 6 Drawing Sheets

U.S. PATENT DOCUMENTS

| | | | |
|---|---|---|---|
| 5,222,980 A | 6/1993 | Gealow | |
| 5,372,573 A | 12/1994 | Habib | |
| 5,429,584 A * | 7/1995 | Chiu | 600/18 |
| 6,045,496 A | 4/2000 | Pacella et al. | |
| 6,454,697 B1 * | 9/2002 | Wang | 600/17 |
| 2003/0233023 A1 | 12/2003 | Khaghani et al. | |

FOREIGN PATENT DOCUMENTS

| | | |
|---|---|---|
| FR | 2 744 021 A1 | 8/1997 |
| FR | 2 751 549 A1 | 1/1998 |
| WO | 02/24254 A2 | 3/2002 |
| WO | 02/24254 A3 | 3/2002 |
| WO | WO 02/24254 * | 3/2002 |

* cited by examiner

PERI-ARTERIAL BLOOD FLOW BOOSTER

FIELD OF THE INVENTION

The present invention relates to a device for improving blood flow. More particularly it relates to a peri-arterial booster for improving blood flow in a blood vessel.

BACKGROUND OF THE INVENTION

Many in western societies suffer from vascular diseases, some of which are diseases of peripheral blood vessels (excluding the heart and brain). An example of such diseases is peripheral occlusive arterial disease (PAOD). In the aforementioned diseases, blood vessels become narrowed or clogged. Most common cause for PAOD is atherosclerosis. Atherosclerosis is a gradual process in which a fibrous, calcified, fatty, or scar tissue builds up, forming plaque that obstructs blood flow to the body periphery. Plaque deposits build up along artery walls and affect blood circulation. When blood flow is severely restricted, intermittent claudication (painful cramping in the leg or hip, particularly when walking), rest pain, ulceration and in extreme cases tissue gangrene ensues which may require, in severe cases, amputation of the affected limb. It is a major cause of life and limb loss, especially in aging population. Several treatment options are currently available, including medical treatment, angioplasty, atherectomy and peripheral bypasses of occluded arterial segments. Currently, no effective drug therapy for opening occluded vessels is available. The success rate of the above-mentioned therapeutic methods is moderate. Furthermore, many patients are not fit for such operations, either on medical grounds or due to anatomical limitations. Also, many cases are not amenable to surgical reconstruction and may end up in gangrene and amputation. Amputation rate in western societies is estimated at about 300 cases per million of population, annually, causing severe suffering and physical disability for patients, as well as imposing heavy financial burdens. To avoid amputation many patients need complex and potentially dangerous operations, between 300-400 vascular reconstructions being performed upon the peripheral arterial tree, per million of population, annually. The present invention provides an alternative treatment to the conventional treatments whereby blood flow is peripherally assisted through the area of impedance. U.S. Pat. No. 5,372,573 (Habib), titled BLOOD FLOW, filed in 1990, discloses a method for improving the blood flow peripherally, through the use of a pump placed in or around a blood vessel supplying blood to a region of increased impedance, and acting to pump blood in the required direction. The pump comprises a housing annularly surrounding a blood vessel, said housing containing a plurality of flexible inflatable containers mounted around the blood vessel and means for effecting sequential inflation and deflation of said containers so as to create a peristaltic pumping effect. A problem arises with the described pump, as it is considerably complicated for assembling, controlling and implanting.

US 20030233023 (Khaghani et al.) discloses a blood circulation assistance device, for location around a blood conduit. The device comprises: an inflatable bladder moveable between a contracted form and an expanded form, for compressing the blood conduit to provide counterpulsation. Pump means in fluid communication with the bladder move the bladder from the contracted form to the expanded form. The pump means comprises a centrifugal impeller rotatable about an axis to effect pumping. The impeller is moveable axially between first and second positions to effect a reversal of the direction of pumping. Control means, in communication with the pump means, is capable of monitoring the cardiac cycle of an individual and triggering the pump means to move the bladder to the expanded form at diastole. An outer cuff, surrounds at least a portion of the bladder, providing an outer limiting extent to the movement of the bladder.

It is an object of the present invention to provide a blood flow booster, which is compact, made up of relatively fewer parts, and fairly simple to implant, if implantation is sought.

Another object of the present invention is to provide a blood flow booster, which is extra-arterial.

Another object of the present invention is to provide a blood flow booster, which is non-occluding.

Another object of the present invention is to provide a blood flow booster, which is ECG sensitive.

Another object of the present invention is to provide a blood flow booster, which is electromechanical.

It is another object of the present invention to provide a blood flow booster, which is also tissue compatible that does not interfere with normal antegrade (i.e. in the correct direction) blood flow.

It is another object of the present invention to provide a blood flow booster having relatively simple structure.

More objects and advantages of the present invention will become apparent from the following detailed description when read in conjunction with the accompanying drawings.

SUMMARY OF THE INVENTION

There is thus provided, in accordance with a preferred embodiment of the present invention, a periarterial blood flow booster apparatus for improving blood pressure and flow, to be implanted around a blood vessel of a patient, the booster comprising:

a pressure applying device comprising at least one balloon, placed alongside a portion of the blood vessel and a restrainer for restraining the balloon and providing counter-forces;

a control console comprising:

an inflating unit for rapidly inflating and deflating the balloon, the inflating unit connected to the balloon;

sensing means for sensing electrocardiograph signals of the patient;

a control unit for controlling the operation of the inflating unit correlating to the electrocardiograph signals detected by the sensing means;

whereby when the balloon is inflated the restrainer forces it to compress the portion of the blood vessel preventing backflow and exerting forces on the blood vessel forcing blood within the portion of the blood vessel to flow antegradely.

Furthermore, in accordance with some preferred embodiments of the present invention, the restrainer is in the form of a sleeve.

Furthermore, in accordance with some preferred embodiments of the present invention, the sleeve is provided with internal protrusion against which the balloon is pressed when inflated, preventing blood backflow effectively acting as a non-return valve.

Furthermore, in accordance with some preferred embodiments of the present invention, the protrusion is in the form of an annular protrusion.

Furthermore, in accordance with some preferred embodiments of the present invention, a sheath covering the balloon, placed between the blood vessel and the balloon will secure the balloon in place and provide an efficient facilitator for balloon replacement.

Furthermore, in accordance with some preferred embodiments of the present invention, the balloon consists of at least two inflatable compartments.

Furthermore, in accordance with some preferred embodiments of the present invention, said at least two inflatable compartments are independently inflatable.

Furthermore, in accordance with some preferred embodiments of the present invention, the sensing means is further provided for sensing blood pressure.

Furthermore, in accordance with some preferred embodiments of the present invention, the control console is implantable within the patient's body.

Furthermore, in accordance with some preferred embodiments of the present invention, the control console is small enough to be carried by the patient.

Furthermore, in accordance with some preferred embodiments of the present invention, the control console is adapted to be attached to a belt to be worn by the patient.

Furthermore, in accordance with some preferred embodiments of the present invention, there is provided a method for improving blood flow and pressure through an occluded blood vessel, said method comprising the steps of:

providing a pressure applying device comprising at least one balloon, placed alongside a portion of the blood vessel and a restrainer for restraining the balloon and providing counter-forces;

providing a control console comprising:

an inflating unit for rapidly inflating and deflating the balloon, the inflating unit connected to the balloon;

sensing means for sensing electrocardiograph signals of the patient;

a control unit for controlling the operation of the inflating unit correlating to the electrocardiograph signals detected by the sensing means;

sensing ECG signals of the patient; and inflating and deflating said at least one balloon in a predetermined rate, correlating to the ECG signals, so as to prevent backflow and compress the portion of the blood vessel in order to force blood within that portion to advance antegradely.

Furthermore, in accordance with some preferred embodiments of the present invention, the blood vessel is an artery.

Furthermore, in accordance with some preferred embodiments of the present invention, the artery is an Iliac artery.

Furthermore, in accordance with some preferred embodiments of the present invention, patient's both Iliac arteries are treated.

Furthermore, in accordance with some preferred embodiments of the present invention, for patients with Heart Failure, the artery is the Descending Aorta.

Furthermore, in accordance with some preferred embodiments of the present invention, a sheath is provided, placed between the blood vessel and the balloon to separate the balloon from the blood vessel and allow safe and fast way of exchanging the balloon when so desired.

BRIEF DESCRIPTION OF THE DRAWINGS

In order to better understand the present invention, and appreciate its practical applications, the following Figures are provided and referenced hereafter. It should be noted that the Figures are given as examples only and in no way limit the scope of the invention. Like components are denoted by like reference numerals.

DETAILED DESCRIPTION OF PREFERRED EMBODIMENTS

Figure 1:
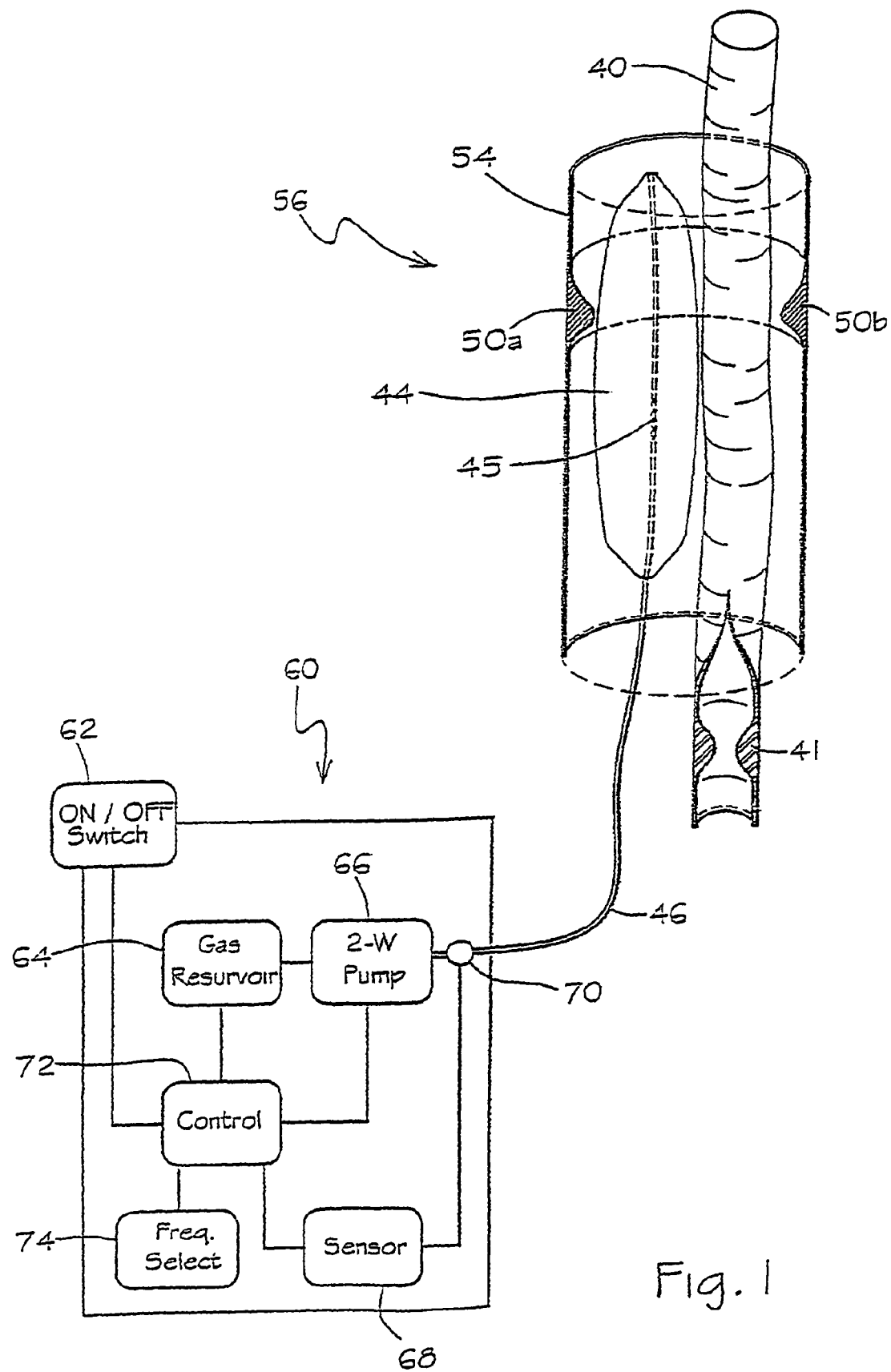
FIG. 1 illustrates a general view of a blood flow booster in accordance with a preferred embodiment of the present invention.

An aspect of the present invention is the provision of an implantable blood flow booster generally comprising the following parts: an inflatable balloon, encircled by a restrainer envelope and a control console connected to and operating the balloon via a pipe in a predetermined manner. The blood flow booster is placed around a blood vessel, e.g. a proximal artery. The inflatable balloon and the restrainer are adapted, upon inflation of the balloon, to provide a boosting effect, increasing the blood flow, and at the same time avoiding backflow of the blood in the blood vessel. The console commands and controls inflation and deflation of the balloon.

An aspect of the present invention is the provision of a device and method for improving blood flow through an obstructed blood vessel by using a blood flow booster coupled to the blood vessel.

The invention will be described further with reference to a treatment of an artery to overcome an obstruction in this artery however it is to understand that the invention is generally applicable to any kind of vasculature.

According to a main aspect of the present invention, there is thus provided a method for improving peripheral blood flow. A pressure applying device, which may be in the form of an inflatable balloon, is used in the present invention to exert pressure onto the artery in a manner which favors forcing the blood to flow downstream (the pressure applying device will be referred to as an inflatable balloon hereinafter, but it is understood and asserted that any other types of pressure applying devices may alternatively be used).

When a single inflatable balloon is used, upon inflation, the balloon occupies the available space within the restrainer and then begins to apply pressure on the blood vessel compressing it against the restrainer. The pressure is applied across a portion of the artery in a gradual manner due to certain adaptation of the restrainer, or a predetermined structural design of the pressure applying device, first blocking an end of that portion (of the artery) upstream and then applying pressure to force blood contained within the portion of the artery to advance downstream, thereby causing the blood to flow in the correct direction. The balloon may be fully or partially inflated (it may be wise to partially deflate the balloon in order to eliminate or minimize potential damage to the blood vessel).

In an embodiment with a balloon having two or more inflatable compartments, which may be fluidly connected to one another or operated separately, upon inflation, the compartment upstream, inflates first causing the collapse of the artery at that position, and the downstream compartment inflates immediately afterwards, compressing against the coupled blood vessel and boosting the blood flow downstream, thus effectively acting as a one way valve.

Habib described in U.S. Pat. No. 5,372,573 a device that uses a plurality of inflatable balloons placed transversely alongside a vein, and inflated sequentially, in order to achieve an increase in for increasing blood flow. However, Habib's device is complicated while the device according to present invention uses a balloon with a restrainer effectively acting as a non-return valve, placed longitudinally alongside and parallel to an artery and squeezing the artery in a predetermined manner. The device is based on the principle of boosting blood flow by increasing pressure, whereas the device described by Habib increases flow only, much like a peristaltic pump. As to Khagani, Khaghani et al. suggest a cardiac assistance device for treatment of acute and end-stage heart failure, while the present invention suggests a booster for blood circulation aimed at assisting blood flow through occluded peripheral blood vessels.

Furthermore, the present invention suggests a design which is aimed at producing force that directs the blood in the right direction, but providing means for ensuring the blocking of backflow, and thus forcing the blood to flow in the right direction. This is achieved by at least two alternative preferred embodiments: The first embodiment involves a balloon with two (or more) inflatable compartments, where a first compartment up stream inflates before the second compartment does, thus first blocking backflow passage, and when the second compartment inflates, blood is forced to move downstream. The second embodiment involves a single balloon that is inflated in a desired direction so that at first the portion that is up stream inflates (blocking backflow) and only then the rest of the balloon inflates.

Reference is now made to the FIG. 1 of the accompanying drawings illustrating a blood flow booster in accordance with a preferred embodiment of the present invention.

A blood flow booster 56 comprises a single inflatable balloon 44, which may be replaceable, placed alongside an artery 40, and a restrainer envelope 54 mounted as a sleeve around the inflatable balloon 44 and the artery segment. The restrainer envelope 54 optionally has a zipper 42 (see FIG. 4), or any other closing means, lengthwise, so as to allow the positioning of the sleeve around the artery, so that implantation does not require invasive arterial operation. The restrainer envelope 54 can be made of a synthetic graft material (like PTFE or Polyester), the interior surface and the exterior surface of the restrainer envelope can be made of two different materials, one for the interior surface and a second material for the exterior surface, for example as described in U.S. Pat. No. 5,372,573 (Habib), titled BLOOD FLOW, filed in 1990, incorporated herein by reference. The interior surface, which is held in contact with the external wall of the artery, is membranous so the wall of the artery will not be damaged, while the exterior surface is be rigid, or at least tougher than the artery, thus the artery will be forced to collapse against the restrainer. The proximal portion of the restrainer envelope consists of a structural design such as an inner annular protrusion, protruding inwardly (in FIG. 1, the annular protrusion is represented by reference no. 50a and 50b, referring to opposing sections of the annular protrusion). An optional radio-opaque marker may be provided on the distal and/or proximal rim of the sleeve to facilitate exact positioning of the balloon (which may also be provided with a radio-opaque marker). The deployment of the balloon can be made using fluoroscopic guidance. The dimensions of the pressure-applying device (the sleeve and the balloon within) may be variable, according to specific patient anatomy (i.e. artery diameter and length of the treated segment) or other needs.

Upon inflation of inflatable balloon 44, the annular protrusion, when the balloon is inflated, serves as a non-return valve preventing backflow. It is understood and asserted that any other types of pressure barriers may alternatively be used. The inflatable balloon 44 is fluidly connected to a hydraulic or pneumatic pressure generator by a pipe 46. The pipe portion that is surrounded by the inflatable balloon consists of several vents 45 through which the balloon is inflated or deflated. The pipe is preferably metallic coated.

Figure 3:
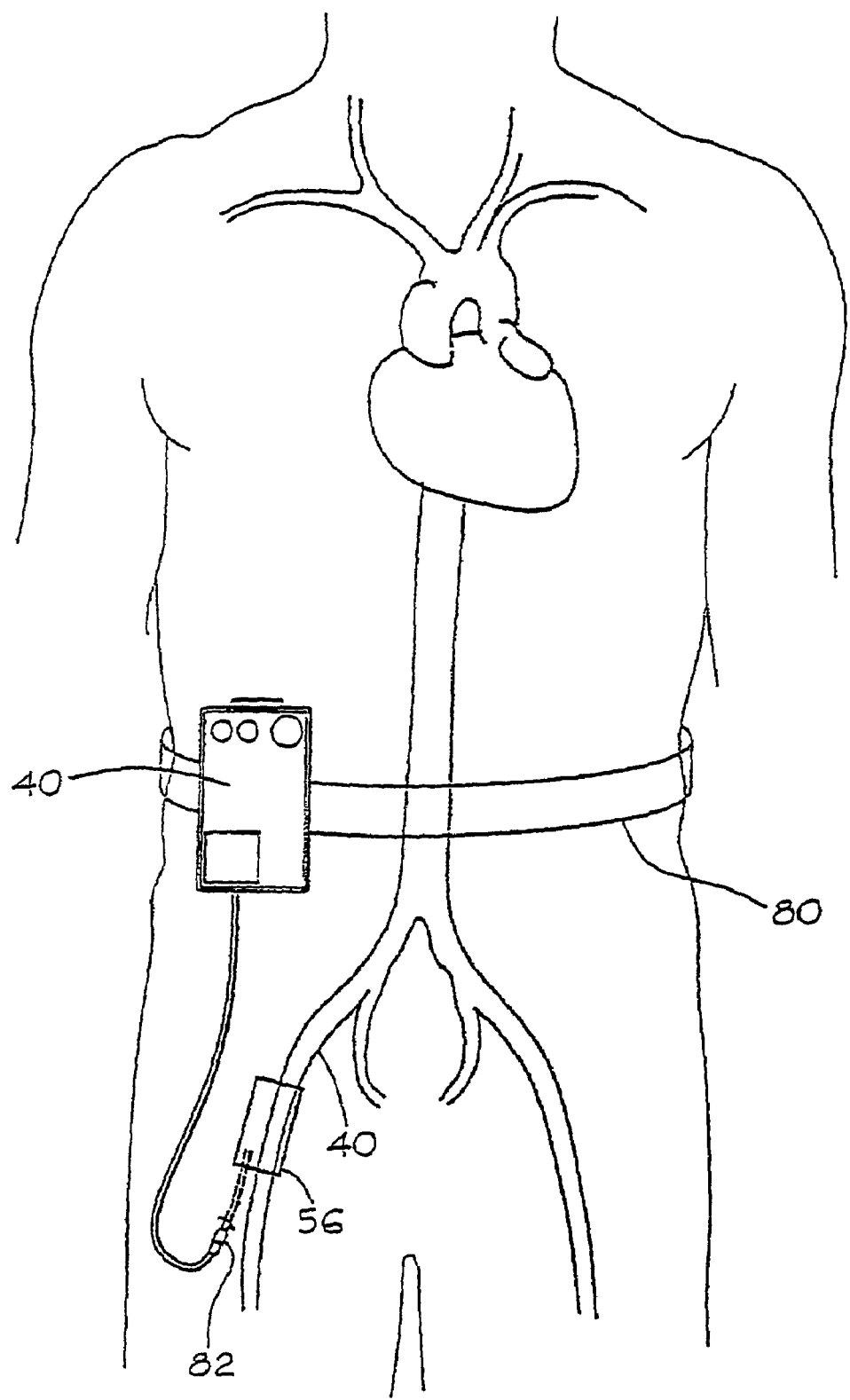
FIG. 3 illustrates a general view of a blood flow booster, in accordance with a preferred embodiment of the present invention, implanted in a patient around an artery, connected to a control console, placed extra corporeal, on a belt about the waist of the patient.

The balloon is operated via a pipe 46 by a control console 60 that may be also implanted inside the patient's body or be placed externally to his body (see for example FIG. 3). The control console 60 comprises a control unit 72 for activating and operating the balloon (inflating and deflating it), by means of an inflating system (for example a two-way pump 66 in a synchronized manner (see detailed explanation hereinafter).

In accordance with FIG. 1, upon inflation of the inflatable balloon 44, the inflatable balloon 44 compresses upon the annular protrusion 50b, thus, the inflatable balloon, compressing upon the artery, causing the artery to press upon the annular protrusion 50a, resulting in obstruction of the artery in such a way that it blocks the upstream portion of the artery, thus preventing upstream flow of blood. Than, the inflatable balloon, as it keeps expanding, gradually compresses the artery 40, first blocking the upstream portion of the artery due to the presence of the annular protrusion 50 and then providing directional forces in the downstream direction (antegrade), thereby, upon inflation of the inflatable balloon 44, boosting of the blood downstream is achieved while preventing backflow of the blood.

Figure 2A:
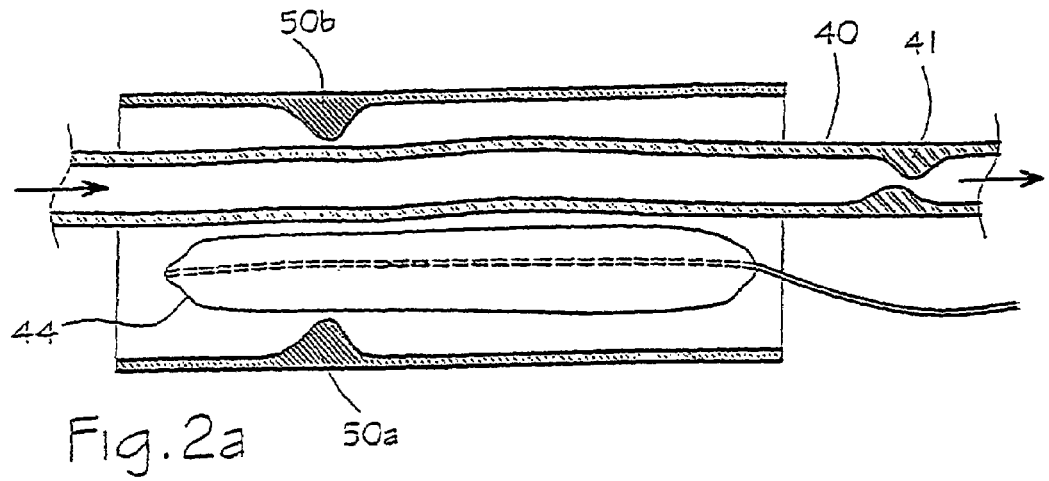
FIG. 2a illustrates a cross-sectional view of a blood flow booster in accordance with a preferred embodiment of the present invention mounted around a blood vessel, in a deflated stage.
Figure 2B:
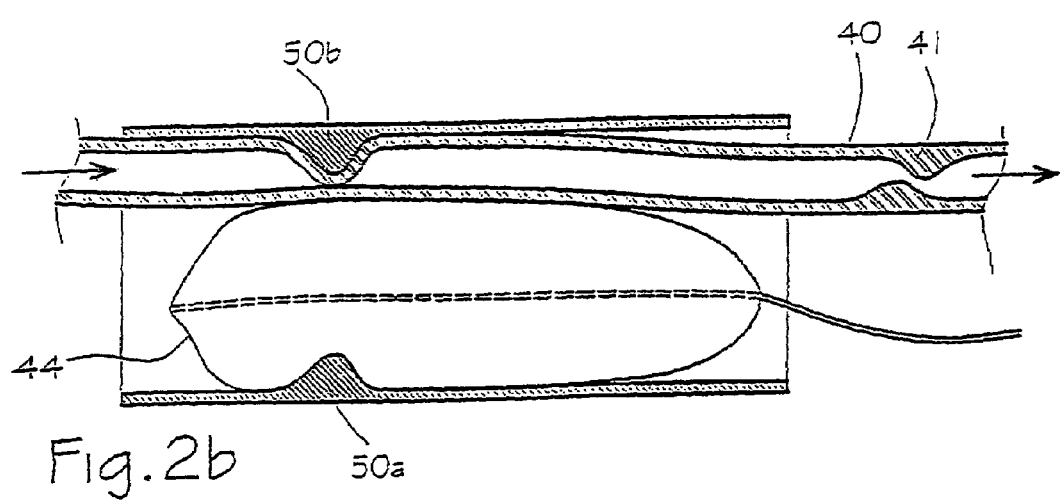
FIG. 2b illustrates a cross-sectional view of a blood flow booster in accordance with a preferred embodiment of the present invention mounted around a blood vessel, in a semi-inflated stage.
Figure 2C:
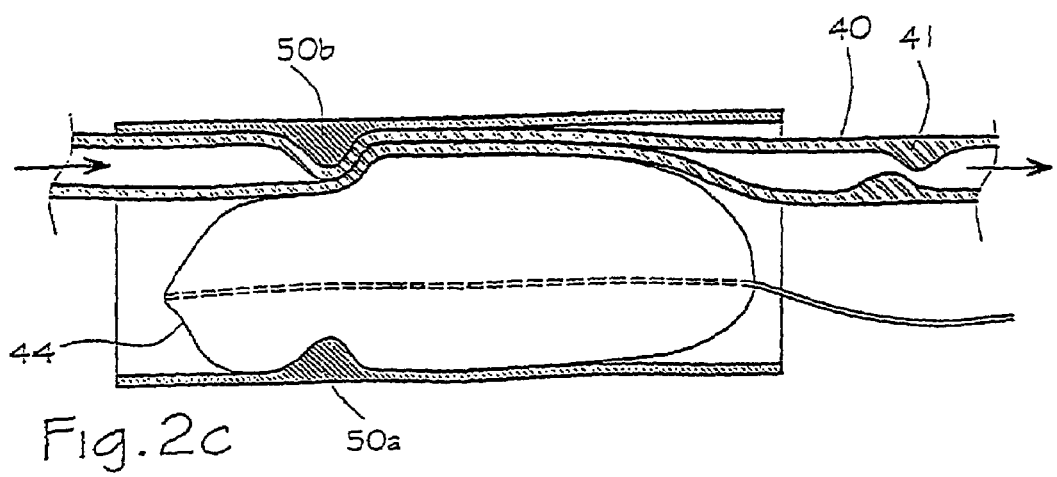
FIG. 2c illustrates a cross-sectional view of a blood flow booster in accordance with a preferred embodiment of the present invention mounted around a blood vessel, in a fully-inflated stage.

FIGS. 2a, 2b and 2c illustrate the modes of operation of the blood flow booster shown in FIG. 1. FIG. 2a illustrates blood flow booster at rest, i.e., the inflatable balloon is deflated. FIG. 2b illustrates state of the blood flow booster balloon 44 and the artery 40 upon semi-inflation of the inflatable balloon 44 (phase 1). Upon inflation, the inflatable balloon 44 compresses against the annular protrusion 50b and the artery, causing the artery to collapse at the contact position with the annular protrusion 50a, which results in the obstruction of the artery in such a way that it blocks the upstream portion of the artery, preventing upstream flow of blood. FIG. 2c illustrates phase 2 of the blood flow booster balloon, i.e., when the inflatable balloon is fully inflated. As the inflatable balloon 92 keeps expanding, it compresses the artery 40, forcing a portion of the artery to collapse under the pressure applied, and consequently forcing the volume of blood within that portion of the artery to advance downstream, thus boosting the blood flow in the downstream direction. The pressure applying device typically is to be positioned upstream with respect to the occluded portion 41 of the artery.

The blood flow booster is controlled and operated by a control console 60 via a pipe 46. The console may be in the form of an implant placed under the skin close to the place where the blood flow booster pressure-applying device is to be positioned, or in the form of a console housed extracorporeally. FIG. 3 shows a general view of a blood flow booster pressure applying device 56, implanted around an artery 40 (however, it can be implanted around any blood vessel), connected to a control console 60, placed extracorporeal, on a belt 80 about the waist of a patient. The control console is connected to a pipe 46, which protrudes from the patient's skin at an exit sit 82, and connected to a corresponding pipe exiting from the console by means of a connector 82.

Referring back to FIG. 1, the control console 60 preferably houses a two-way hydraulic or pneumatic pump 66, a gas (or liquid) reservoir 64 for supplying gas (or liquid) for inflating the balloon, a control unit 72, sensor 68 for sensing ECG (electrocardiograph) signals corresponding to the cardiac activity of the patient (and or pressure sensor for sensing the blood pressure within the artery for safety reasons, in order to control and limit the maximal pressure buildup within the artery caused by the operation of the blood flow booster), optional frequency selector 74 (for manually setting rate) and an on/off switch 62 for activating or deactivating the system. It is noted that similar consoles are currently in use for cardiovascular support of failing hearts (for example consider the intra aortic balloon pump—IABP-consoles marketed by Arrow International Inc., Reading Pa., under the brand names Arrow Transact™ and ACAT®1 PLUS, or Datascope Inc. NY, USA, model brand name System 98TX). Note that IABPs are used intra-aortically to reverse blood flow in order to enhance blood flow to the coronary arteries as opposed to the present invention which deals with boosting of blood flow antegradely.

The frequency selector 74 is optionally provided in order to allow the physician to set a rate related either to the patient's heart rate or to a different pre-selected rate.

Figure 5A:
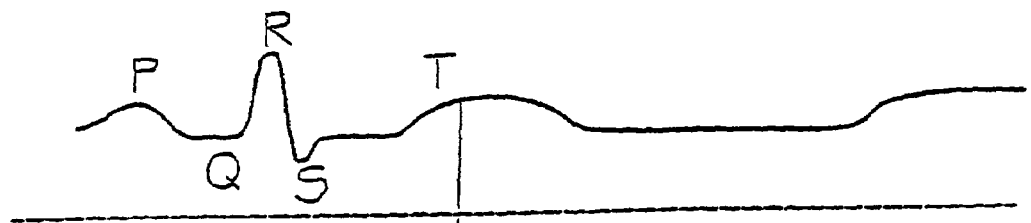
FIG. 5a shows a typical electrocardiogram of a single heartbeat.
Figure 5B:
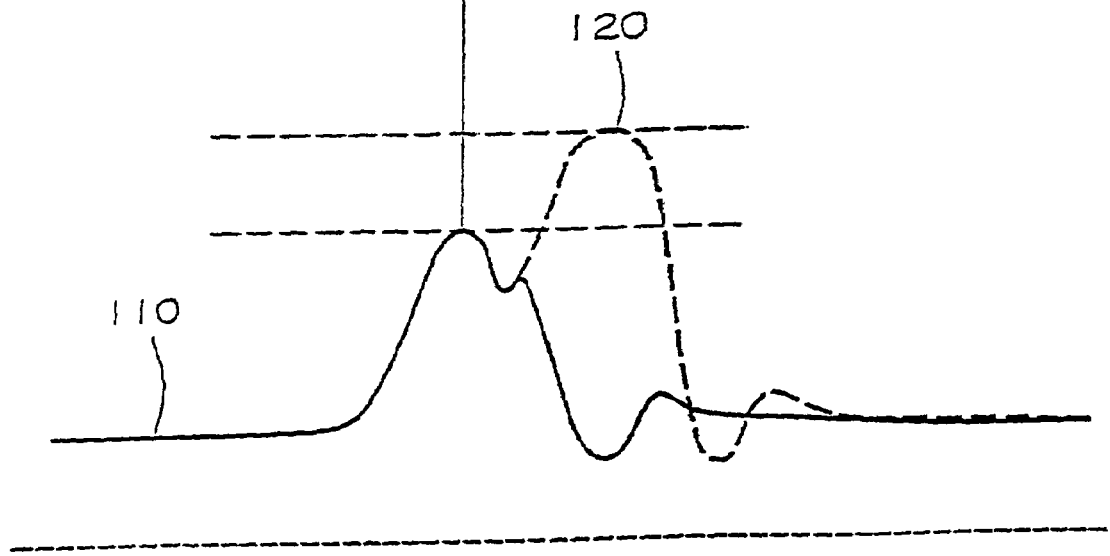
FIG. 5b illustrates the pressure front propagation with respect to the heartbeat shown in FIG. 5a. The boosted pressure front is shown in the form of a dashed-line.

The console controls the inflation and deflation of the balloon system in a predetermined rate, volume and pressure. ECG signals of the patient are monitored (via sensor 68) and inflation timing is synchronized to occur at the diastolic phase of blood flow, if the rate is to relate in a 1:1 relation to the patient's heart rate, or in any other selected rate (set by the physician using the frequency selector 74). ECG signals of the patient are optionally conducted to the console over the pipe, which may be made to conduct electric signals. The control unit 72, processes the input from the sensor, and accordingly activates the blood flow pressure-applying device 56. FIG. 5 illustrates an electrocardiogram output (FIG. 5a), and a simultaneous arterial pressure output (FIG. 5b) with a boosted pressure wave, represented by the dashed line. FIG. 5b illustrates a normal arterial pressure 110 in accordance to the electrocardiogram. Arterial pressure reading 112 indicates the increase in the arterial pressure due to boosting by the blood flow booster of the present invention.

An arterial blood pressure sensor may be incorporated within the restrainer envelope at the upstream end and link to the console. Other pressure sensor may be placed within the treated artery further downstream with respect to the occluded portion.

In a blood flow booster having an arterial pressure detector, when the console detects that the arterial blood pressure is not synchronized with the ECG, the console activates the pneumatic pressure generator (although any pressure generator is applicable) and thus the pneumatic fluid will inflate the balloon. This will cause boosting of blood flow at the right direction (downstream) and the arterial pressure and flow will increases.

Figure 4:
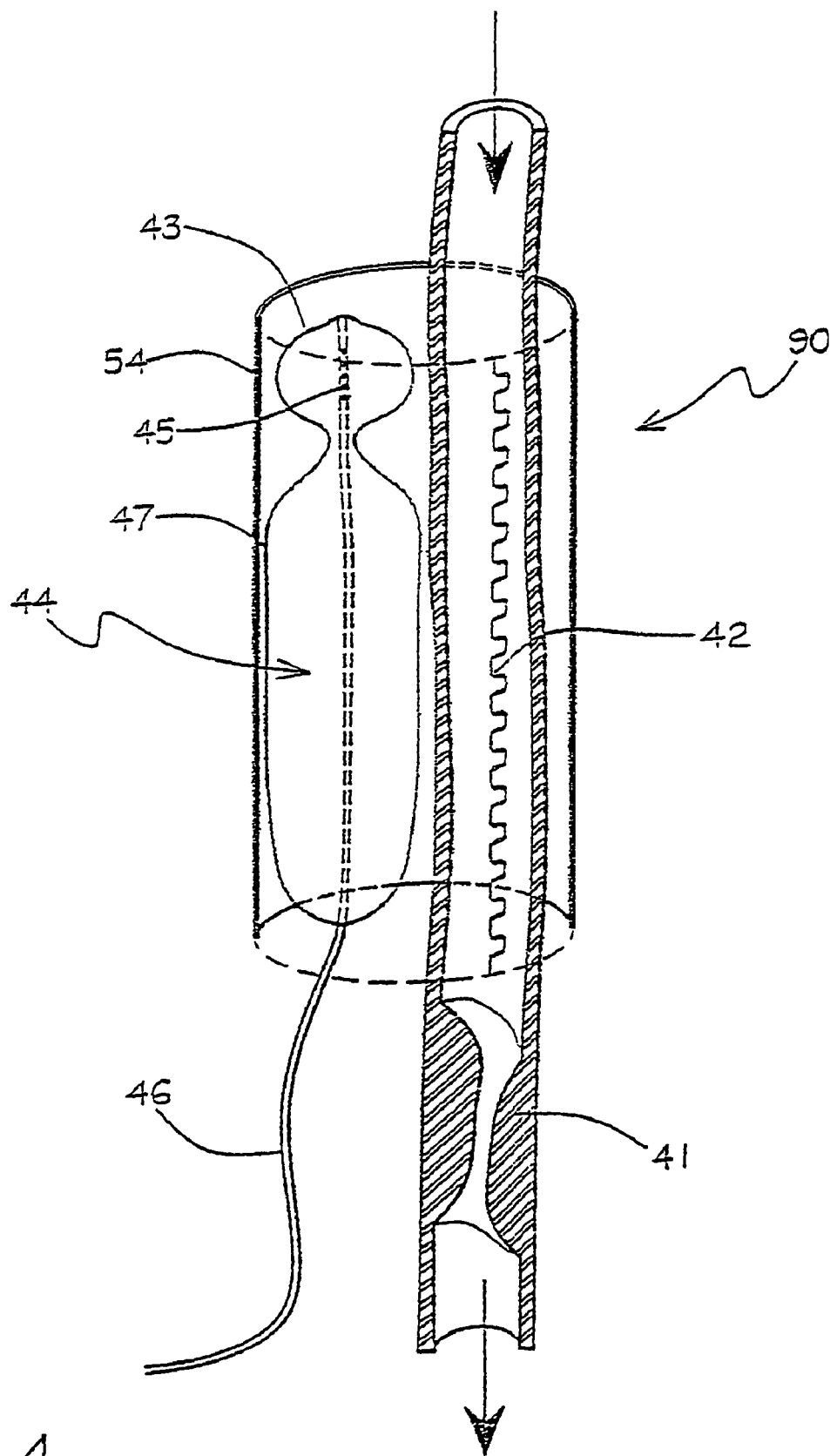
FIG. 4 illustrates general view of a blood flow booster in accordance with another preferred embodiment of the present invention.

Reference is now made to the FIG. 4 of the accompanying drawings illustrating blood flow booster in accordance with another preferred embodiment of the present invention.

A blood flow booster pressure applying device 90 comprises an inflatable balloon 20 comprises an inflatable balloon with two or more inflatable compartments (43, 47) (It is understood and asserted that any other types of pressure applying devices may alternatively be used), placed alongside artery 40, and a restrainer envelope 54 mounted as a sleeve around both the inflatable balloon 44 and the artery 40.

The inflatable balloon 44 is connected via pipe 46, which may preferably be metallic coated (in order to be able to convey ECG signals to the control console, to a hydraulic or a pneumatic pressure generator (preferably a pneumatic pressure as it has a relatively fast response time and power dissipation in terms of heat is relatively small), located within the control console 60 (placed outside the patient's body or inside it, in case of an implant).

The inflatable balloon 44 consists of an occluding balloon 43 for providing occlusion to possible backflow of the blood during operation of the pressure applying device, and of a longer pressure applying balloon 47. The two compartments may be fluidly communicating between each other or independently operated. The occluding balloon 43 is placed upstream with respect to the pressure applying balloon 47. The balloon compartments are inflatable via pipe 46. In the embodiment shown in FIG. 4 a portion of the pipe 46, surrounded by the occluding balloon, consists of several vents 45 located within the occluding balloon compartment. Thus, upon inflation, the occluding balloon 43, inflates first compressing the adjacent artery portion, and then the pressure applying balloon inflates to force blood found in the portion of the artery which is adjacent the pressure applying balloon downstream.

The blood flow booster pressure-applying device 90 is implanted on an arterial segment, preferably implanted upstream, near an occluding lesion 41 found within the blood vessel Upon activation of the blood flow booster, the hydraulic or pneumatic pressure generator, preferably the pneumatic pressure generator, supplies inert gas, preferably Helium, to the inflatable balloon through the vents of the pipe (45 in FIG. 1, 23 in FIG. 4), thus the balloon is inflated.

Figure 6:
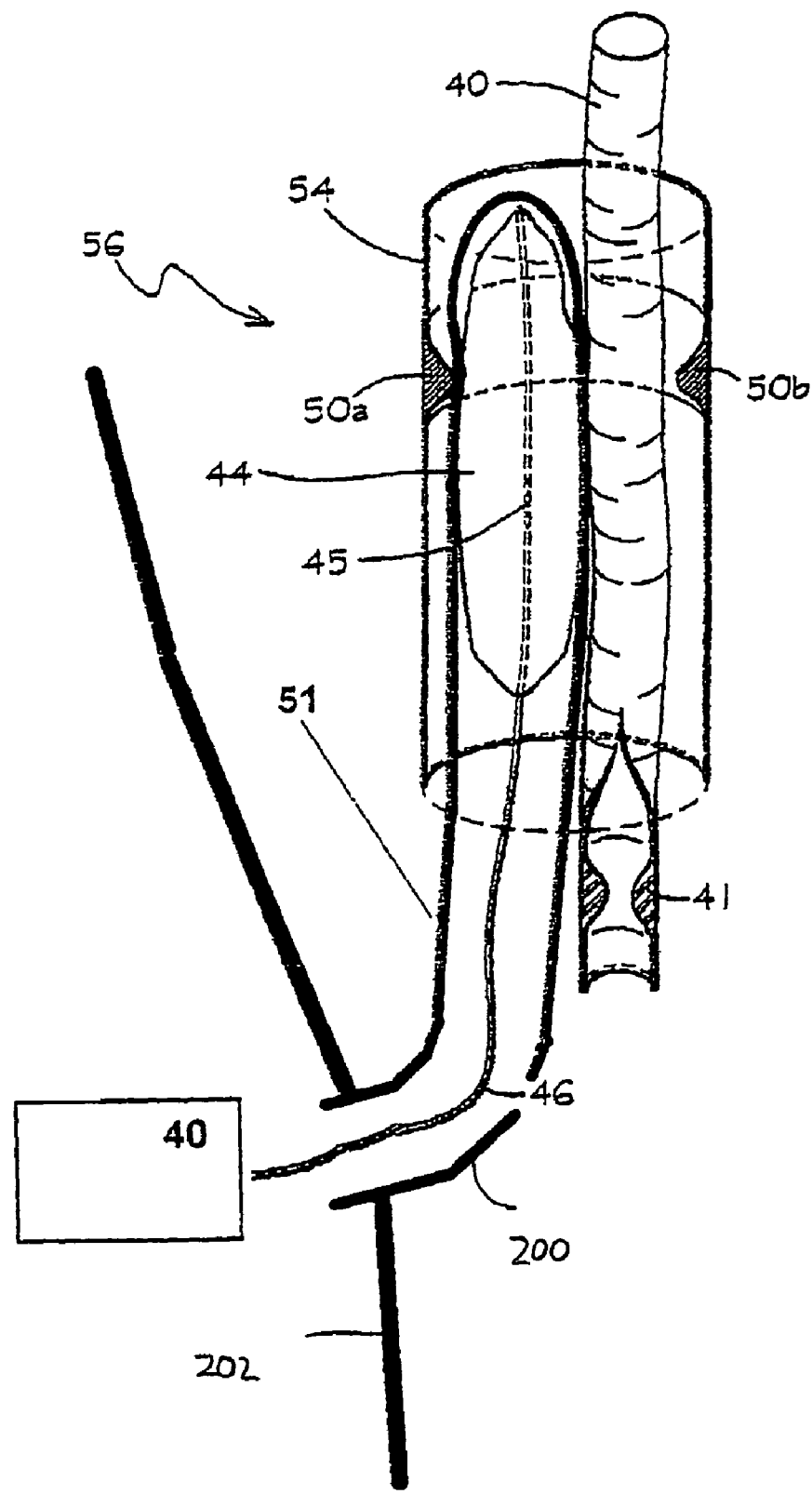
FIG. 6 illustrates a blood flow booster in accordance with another preferred embodiment of the present invention.

A sheath 200 covering the balloon (51 in FIG. 6) can be placed between the blood vessel and the balloon. It will secure the balloon in place and provide an efficient facilitator for balloon replacement. The sheath separates the balloon from the tissue and connects it directly with the extracorporeal space. The end of the sheath may protrude from the patient's skin 202 or it may lie below the skin. The provision of a sheath allows separation of the balloon from the blood vessel and allows safe and fast way of exchanging the balloon when so desired. The end of the sheath may be left outside the skin (as shown in FIG. 6) or below it.

According to the present invention, blood flow booster increases distal blood pressure and flow across an obstruction. Placing of the blood flow booster outside of the blood vessel is advantageous, as it requires a minimally-invasive surgery with no thrombotic sequella anticipated. The blood flow booster according to the present invention has a relatively simple structure. It is relatively easy to use and it is relatively easy to remove and replace the balloon system (this may be carried out using known catheterization methods). The present invention provides an alternative treatment to the conventional treatments whereby blood flow is assisted through the area of impedance; this has the potential of saving many limbs and lives.

The apparatus and method of the present invention may be implemented in Congestive Heart Failure (CHF) cases, where the pressure-applying device is placed around the descending Aorta in the chest. In this case the size of the sleeve and the corresponding balloon will be matched to the diameter of the Aorta, which is larger than the Iliac artery. The present booster may allow patients with CHF the use of a portable, extra-arterial heart assist device, which is not available yet. Typically the effective length of the pressure applying device is correlated to the diameter of the artery: the volume of blood to be compressed forward is represented by the formula $V=\pi r^2 L$, where r is the radius of the artery and L is the effective length of the pressure applying device. The volume flow equals to VN/t, where t is the period of the pulse and N is the number of pulses. These parameters affect the blood pressure distal to the occluded segment.

The following tables summarize results of experiments with the Booster device, both IN VITRO on a synthetic model of a pressurized blood vessel and IN VIVO in experimental animals with constriction of an artery.

Experiments of the Peri-arterial Blood Flow Booster (Values are averages of series of measurements)

1. Feasibility study of increasing pressure in a pressurized closed tube IN VITRO:

| Basic pressure (mm Hg) | Peak Pressure (mm Hg) | Difference from Baseline (mm Hg) | Percent Change (%) |
|---|---|---|---|
| 50 | 73 | 23 | 46 |
| 60 | 108 | 48 | 80 |
| 85 | 175 | 90 | 105 |
| 100 | 230 | 130 | 130 |

2. Efficacy of the Non-Return Valve Mechanism IN VITRO using various balloon volumes:

| Balloon Volume (percent) | Peak Upstream Pressure (mm Hg) | Peak Downstream Pressure (mm Hg) | Pressure Gradient (mm Hg) |
|---|---|---|---|
| 30 | 48 | 48 | 0 |
| 60 | 96 | 96 | 0 |
| 75 | 84 | 120 | 36 |
| 100 | 48 | 204 | 156 |

3. IN VIVO Boosting Experiments, Pressure Increase distal to an arterial constriction:

| | Basic Systolic Blood Pressure (mm Hg) | Distal Pressure during boosting (mm Hg) | Pressure Increase (mm Hg) |
|---|---|---|---|
| Intact artery | 117 | 145 | 28 |
| Constricted artery | 75 | 115 | 40 |

4. IN VIVO Boosting Experiments, Flow Increase distal to an arterial constriction:

| | Basic Flow (ml/min) | Flow during Boosting (ml/min) | Flow Increase (ml/min) | Percent Change (%) |
|---|---|---|---|---|
| Intact artery | 93 | 107 | 14 | 15 |
| Constricted artery | 39 | 60 | 21 | 53 |

In summary, these experiments show that the Booster device increases blood pressure across a constriction up to 40 mm of Hg, and blood flow up to 53% from baseline. These increases are sufficient to improve the condition of a patient.

The above description should not be construed as limitation on the scope of the invention, but rather an exemplification thereof. Many other variations are possible. For example a variety of control arrangements are possible. One or more pressure sensors for sensing blood pressure may be incorporated. Such sensors may be used to supply information to the console, which controls the operation of the blood flow booster in accordance with the arterial pressure.

The invention is expected to find applications in other clinical or veterinary conditions involving decrease of blood flow due to obstruction of blood vessels.

It should be clear that the description of the embodiments and attached Figures set forth in this specification serves only for a better understanding of the invention, without limiting its scope as covered by the following Claims or their equivalents It should also be clear that a person skilled in the art, after reading the present specification could make adjustments or amendments to the attached Figures and above described embodiments that would still be covered by the following Claims or their equivalents.

The invention claimed is:

1. A peri-arterial blood flow booster apparatus, for comprising:
   a pressure-applying device comprising:
      a restrainer envelope having an upstream end and a downstream end, and an interior surface defining an interior for receiving a blood vessel and a protrusion fixedly disposed on the interior surface; and
      a balloon disposed in the interior of the restrainer envelope for placing alongside a portion of the blood vessel, having two or more portions comprising an upstream portion disposed in the restrainer envelope interior extending from said protrusion towards the upstream end and a downstream portion disposed in the interior extending from said protrusion towards the downstream end, and
   a control console comprising
      an inflating unit for rapidly inflating and deflating the balloon, the inflating unit being connected to the balloon,
      sensing means for sensing electrocardiograph signals of a the patient, and
      a control unit for controlling the inflating unit in correlation with the electrocardiograph signals detected by the sensing means;
      wherein the downstream portion of the balloon extends further downstream from the protrusion than the upstream portion extends upstream from the protrusion such that upon inflation of the upstream portion blood backflow is prevented, and upon inflation of the downstream portion blood is forced to flow downstream.

2. The apparatus of claim 1, wherein the restrainer envelope is a sleeve.

3. The apparatus of claim 1, wherein the protrusion is an annular protrusion.

4. The apparatus of claim 1, wherein the sensing means further comprises means provided for sensing blood pressure.

5. The apparatus of claim 1, wherein the control console is implantable within the patient's body.

6. The apparatus of claim 1, wherein the control console is configured sufficiently small in size so as to be portable.

7. The apparatus of claim 6, wherein the control console is configured sufficient to be attached to a belt to be worn by a patient.

8. The apparatus of claim 1, further comprising provided with a sheath provided over the at least one balloon.

9. A method for improving blood flow and pressure through an occluded blood vessel of a patient, comprising:
 providing a pressure-applying device comprising
  a restrainer envelope having an upstream end and a downstream end, and an interior surface defining an interior for receiving a blood vessel and a protrusion fixedly disposed on the interior surface;
  a balloon disposed in the interior of the restrainer envelope for placing alongside a portion of the blood vessel, having two or more portions comprising an upstream portion disposed in the restrainer envelope interior and extending from said protrusion towards the upstream end and a downstream portion disposed in the restrainer envelope interior extending from said protrusion towards the downstream end,
  wherein the downstream portion of the balloon extends further downstream from the protrusion than the upstream portion extends upstream of the protrusion such that upon inflation of the upstream portion, blood backflow is prevented, and upon inflation of the downstream portion blood is forced to flow downstream, and
 affixing the pressure-applying device to a portion of a peripheral blood vessel of the patient;
 providing a control console comprising
  an inflating unit for rapidly inflating and deflating the at least one balloon, the inflating unit being connected to the balloon,
  sensing means for sensing electrocardiograph signals of a the patient, and a control unit for controlling the inflating unit in correlation with the electrocardiograph signals detected by the sensing means;
 sensing the electrocardiograph signals of the patient;
 and inflating and deflating said at least one balloon at a predetermined rate, in correlation with the electrocardiograph signals.

10. The method of claim 9, wherein the restrainer envelope is a sleeve.

11. The method of claim 9, wherein the protrusion is an annular protrusion.

12. The method of claim 9, wherein the sensing means further comprises means for sensing blood pressure.

13. The method of claim 9, further comprising implanting the control console within the patient's body.

14. The method of claim 9, wherein the control console is configured sufficiently small in size so as to be portable.

15. The method of claim 14, wherein the control console is configured sufficient to be attached to a belt to be worn by the patient.

16. The method of claim 9, wherein the blood vessel is an artery.

17. The method of claim 16, wherein the artery is an iliac artery.

18. The method of claim 17, wherein both of the patient's iliac arteries are treated.

19. The method of claim 16. wherein the artery is in the descending aorta in the chest of the patient.

20. The method of claim 9, further comprising providing a sheath covering the at least one balloon, the said sheath being placed between the blood vessel and the at least one balloon.

* * * * *